(12) United States Patent
Chen et al.

(10) Patent No.: US 8,057,844 B2
(45) Date of Patent: Nov. 15, 2011

(54) METHODS FOR COATING IMPLANTABLE MEDICAL DEVICES

(75) Inventors: Yung-Ming Chen, Cupertino, CA (US); Henjen Ho, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/473,211

(22) Filed: May 27, 2009

(65) Prior Publication Data

US 2009/0238949 A1  Sep. 24, 2009

Related U.S. Application Data

(62) Division of application No. 10/747,996, filed on Dec. 29, 2003, now Pat. No. 7,563,324.

(51) Int. Cl.
- B05C 11/10 (2006.01)
- B05C 1/00 (2006.01)
- A61L 33/00 (2006.01)
- B05D 1/28 (2006.01)

(52) U.S. Cl. .. 427/2.24; 427/2.1; 427/2.25; 427/428.01; 427/430.1; 118/264; 118/270; 118/268; 118/269; 118/200; 118/232; 118/422; 118/429

(58) Field of Classification Search .......... 427/2.1, 427/2.24, 2.25, 428.01, 249, 430.1; 118/200, 118/232; 623/1.45, 1.46
See application file for complete search history.

(56) References Cited

U.S. PATENT DOCUMENTS

| | | | |
|---|---|---|---|
| 4,976,615 A | 12/1990 | Kravitz | |
| 5,136,968 A | 8/1992 | Sarada et al. | |
| 5,658,084 A * | 8/1997 | Wirt | 401/132 |
| 5,866,210 A * | 2/1999 | Rosynsky et al. | 427/294 |
| 6,395,326 B1 * | 5/2002 | Castro et al. | 427/2.24 |
| 6,739,033 B2 * | 5/2004 | Hijlkema et al. | 29/508 |
| 6,971,813 B2 * | 12/2005 | Shekalim et al. | 401/208 |
| 7,056,591 B1 | 6/2006 | Pacetti et al. | |
| 7,198,675 B2 | 4/2007 | Fox et al. | |
| 7,220,816 B2 | 5/2007 | Pacetti et al. | |
| 7,258,891 B2 | 8/2007 | Pacetti | |
| 7,323,209 B1 * | 1/2008 | Esbeck et al. | 427/2.25 |
| 7,323,210 B2 | 1/2008 | Castro et al. | |
| 7,338,557 B1 | 3/2008 | Chen et al. | |
| 7,416,609 B1 | 8/2008 | Madriaga et al. | |
| 7,435,788 B2 | 10/2008 | Pacetti et al. | |
| 2003/0196596 A1 * | 10/2003 | Nishi et al. | 118/300 |
| 2003/0215564 A1 | 11/2003 | Heller et al. | |
| 2005/0074544 A1 * | 4/2005 | Pacetti et al. | 427/2.1 |

OTHER PUBLICATIONS

Research Disclosure Database No. 434009,, Drug Loading Device for Drug Delivery or Coated Stent, published Jun. 2000, Mason publications.*
U.S. Appl. No. 10/255,913, filed Sep. 26, 2002, Tang et al.
U.S. Appl. No. 10/317,435, filed Dec. 11, 2002, Hossainy et al.

* cited by examiner

*Primary Examiner* — Timothy Meeks
*Assistant Examiner* — Cachet Sellman
(74) *Attorney, Agent, or Firm* — Squire, Sanders & Dempsey (US) LLP

(57) ABSTRACT

Methods for coating an implantable medical device, such as a stent, are provided.

8 Claims, 10 Drawing Sheets

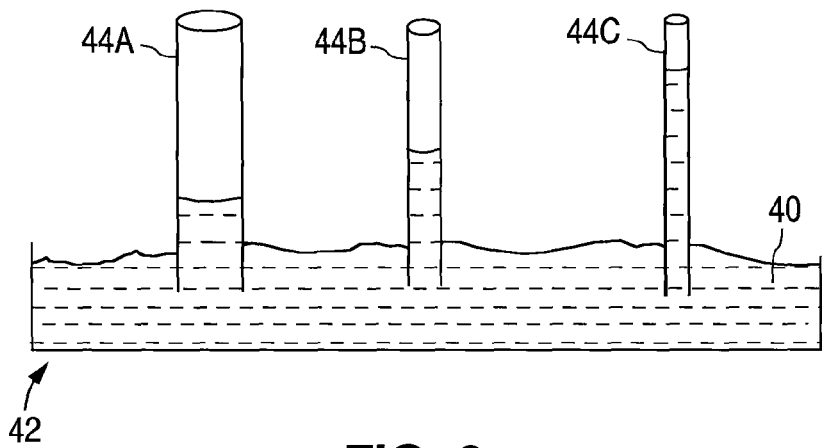
FIG. 6
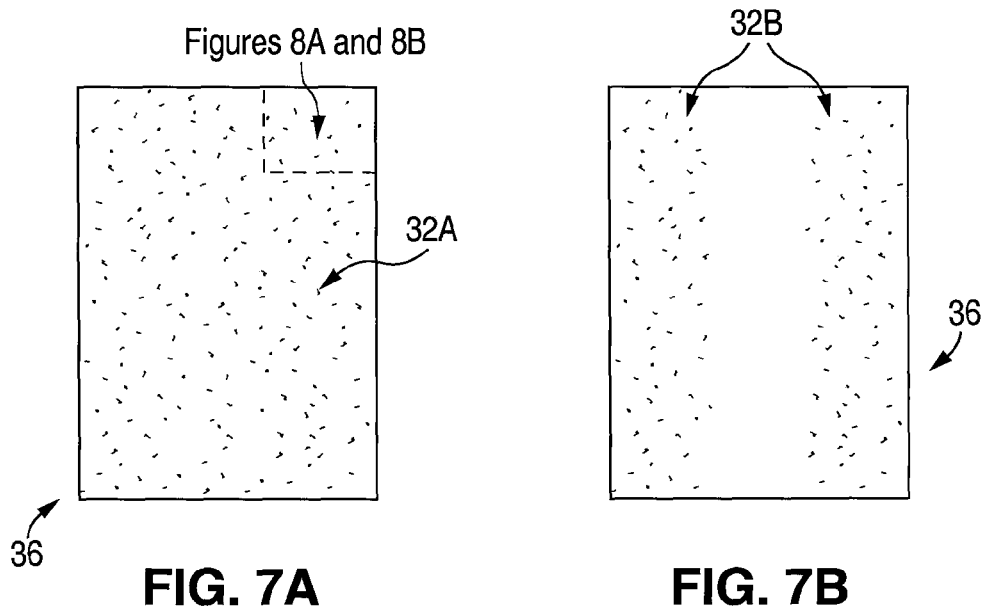
FIG. 7A  FIG. 7B
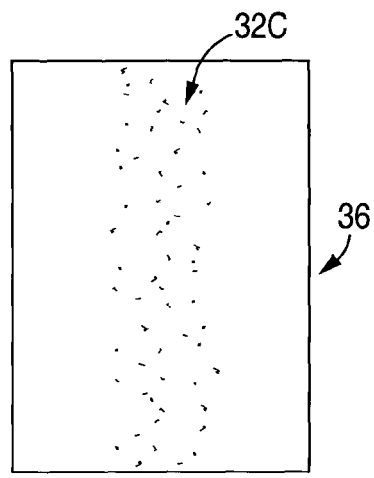
FIG. 7C

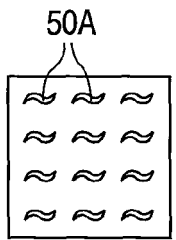
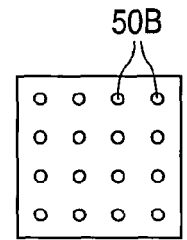
FIG. 8A  FIG. 8B
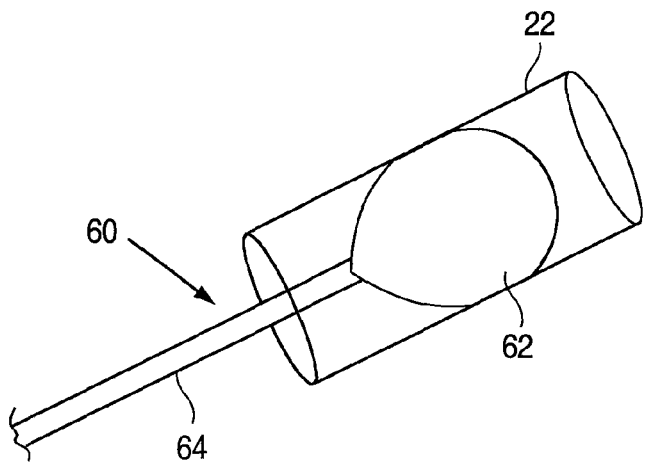
FIG. 9
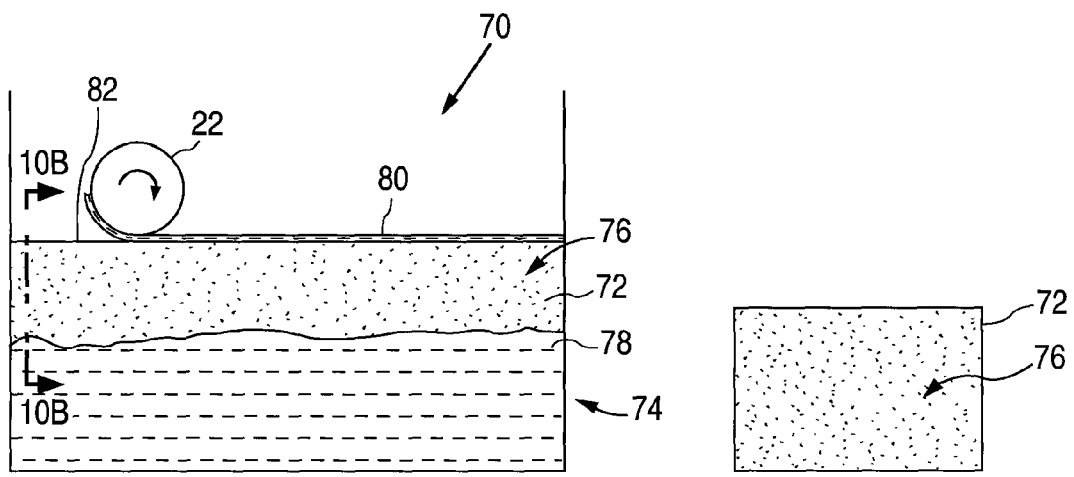
FIG. 10A  FIG. 10B

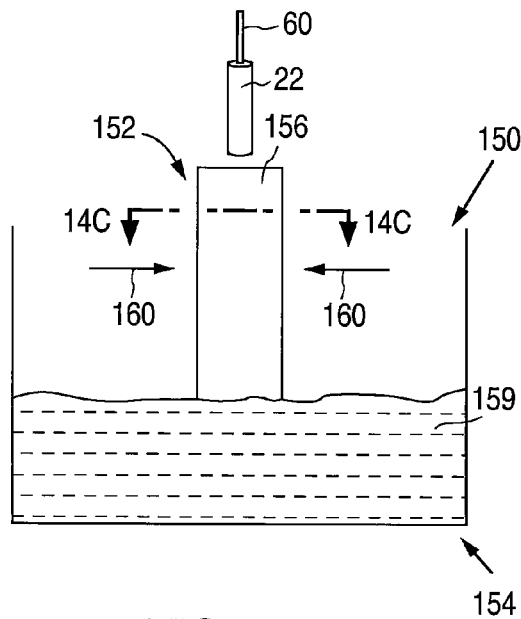
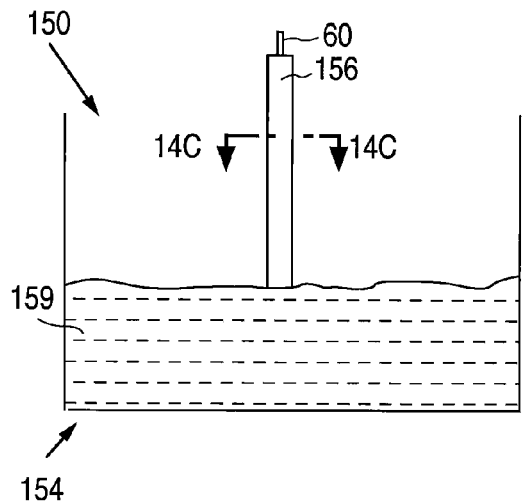
FIG. 14A
FIG. 14B
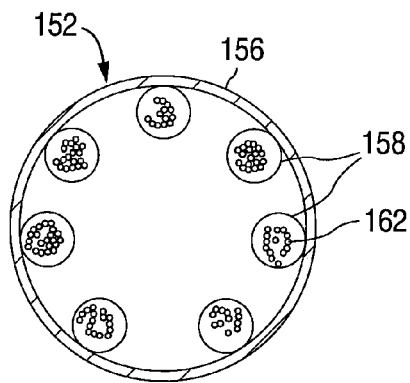
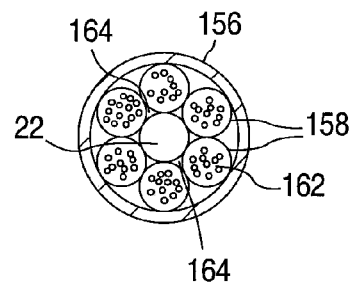
FIG. 14C
FIG. 14D

METHODS FOR COATING IMPLANTABLE MEDICAL DEVICES

This application is a divisional application of U.S. Ser. No. 10/747,966, now U.S. Pat. No. 7,563,324, filed Dec. 29, 2003, hereby incorporated by reference in its entirety as if fully set forth herein, including the drawings.

BACKGROUND OF THE INVENTION

1. Field of the Invention

This invention relates to a system for coating an implantable medical device, such as a stent, and a method of coating a device using the system.

2. Description of the Background

Blood vessel occlusions are commonly treated by mechanically enhancing blood flow in the affected vessels, such as by employing a tubular implantable medical device known as a stent. Stents act as scaffoldings, functioning to physically hold open and, if desired, to expand the wall of the passageway. Stents are capable of being compressed, so that they can be inserted through small lumens via catheters, and then expanded to a larger diameter once they are at the desired location.

FIG. 1 illustrates a conventional stent 10 formed from a plurality of structural elements including struts 12 and connecting elements 14. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that can produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

As noted above, one of the methods of applying a drug composition to a stent involves spraying the composition onto the stent. The composition can be atomized to produce small droplets. Atomization is used because the droplet size can be made smaller than the size of the stent's structural elements, thus enabling a substantially conformal coating. However, there are potential shortcomings associated with a spray coating process. For instance, many of the drugs and polymers that are applied to stents are toxic when inhaled by humans. As the polymeric drug solutions are atomized, therefore, great care must be taken to avoid occupational exposure to the personnel conducting the process. Hoods, glove boxes, enclosures, and shrouds can be used to prevent toxic aerosol inhalation, but at a cost of decreased efficiency and increased expenditures on equipment. In light of these safety and manufacturing concerns, a stent coating method that avoids atomization of the coating can be advantageous.

Another disadvantage of a spray coating process is that the transfer efficiency can be comparatively low. Only droplets which fall onto the stent's structural elements are incorporated into the coating. If the spray pattern is larger than the stent, much of the spray can be wasted. Moreover, the stent's body can have a number of open spaces or gaps between the structural elements that allow the spray to pass through, and therefore be unused. The components of the coating compositions can be very expensive. For instance, many of the drugs applied to stents are small molecule agents or biologically derived substances such as peptides and gene therapy agents that are very costly. A stent coating method which transfers the coating solution in a more direct manner to the stent structure would therefore have a manufacturing cost advantage.

The dipping or spraying of the composition onto the stent can result in a complete coverage of all stent surfaces, i.e., both luminal (inner) and abluminal (outer) surfaces, with a coating. However, from a therapeutic standpoint, drugs need only be released from the abluminal stent surface, and possibly the sidewalls. Moreover, having a coating on the luminal surface of the stent can have a detrimental impact on the stent's deliverability as well as the coating's mechanical integrity. A polymeric coating can increase the coefficient of friction between the stent and the delivery balloon. Additionally, some polymers have a "sticky" or "tacky" consistency. If the polymeric material either increases the coefficient of friction or adherers to the catheter balloon, the effective release of the stent from the balloon after deflation can be compromised. Adhesive, polymeric stent coatings can also experience extensive balloon sheer damage post-deployment, which could result in a thrombogenic luminal stent surface. Accordingly, there is a need to eliminate or minimize the amount of coating that is applied to the inner surface of the stent. Reducing or eliminating the polymer from the stent luminal surface also means a reduction in total polymer load, which is a desirable goal for optimizing long-term biocompatibility of the device.

A method for preventing the composition from being applied to the inner surface of the stent is by placing the stent over a mandrel that fittingly mates within the inner diameter of the stent. A tubing can be inserted within the stent such that the outer surface of the tubing is in contact with the inner surface of the stent. A tubular mandrel that makes contact with the inner surface of the stent can cause coating defects in spraying and dipping application processes. A high degree of surface contact between the stent and the support apparatus can provide regions in which the sprayed or dipped liquid composition can flow, wick, and collect. As the solvent evaporates, the excess composition hardens to form excess coating at and around the contact points between the stent and the support apparatus. Upon the removal of the coated stent from the mandrel, the excess coating may stick to the mandrel, thereby removing some of the coating from the stent in the form of peels as shown in FIG. 2, or leaving bare areas as shown in FIG. 3. Alternatively, as illustrated in FIG. 4, the excess coating may stick to the stent, thereby leaving excess coating as clumps or pools on the struts or webbing between the struts. These types of defects can cause adverse biological responses after the coated stent is implanted into a biological lumen.

Accordingly, the present invention provides a system and method for coating an implantable medical device that addresses these concerns and others needs as are apparent to one having ordinary skill in the art.

SUMMARY OF THE INVENTION

In accordance with one aspect of the invention a system for coating an implantable medical device with a coating composition is provided, including a reservoir holding a coating composition, an applicator including a coating surface and a porous region in fluid communication with the coating composition in the reservoir, wherein the porous region is capable of conveying the coating composition from the reservoir to the coating surface, and a support element to support an implantable medical device in close proximity to or in contact with the coating surface of the applicator. In one embodiment, the applicator includes a tubular body. In another embodiment, the coating surface comprises a flat substrate on which the device can be placed. In yet another embodiment, the applicator is made from a ceramic or polymeric material.

In accordance with another aspect of the present invention, an applicator for coating an implantable medical device with a coating composition is provided, comprising a hollow tubular body having a bore configured to receive an implantable medical device; and a plurality of fibers disposed along the bore of the body, the fibers configured to receive a coating composition to apply the coating composition to the implantable medical device.

In accordance with a further aspect, a system for coating an implantable medical device with a coating composition is provided, including a reservoir holding a coating composition, and an applicator including a coating surface and a porous region in communication with the coating composition in the reservoir, wherein the porous region is capable of loading the coating surface with the coating composition from the reservoir by capillary action. In one embodiment, the system further comprises a support element to support an implantable medical device in close proximity to or in contact with the coating surface.

In accordance with yet another aspect, a method of coating an implantable medical device is provided, including positioning a part of an applicator in a reservoir having a coating composition, the applicator including a coating surface and a porous region capable of conveying the coating composition from the reservoir to the coating surface, allowing the coating composition to be conveyed to the coating surface, and transferring at least some of the coating composition from the coating surface onto an implantable medical device.

In accordance with another aspect of the invention, a method of coating an implantable medical device is provided, including exposing a portion of an applicator to a coating composition, the applicator including a coating surface, allowing a layer of the coating composition to be formed on the coating surface of the applicator by capillary action, and transferring at least some of the coating composition from the coating surface onto an implantable medical device.

BRIEF DESCRIPTION OF THE FIGURES

FIG. 6 is an illustration of capillary tubes partially filled by a liquid as a result of capillary action;

FIGS. 7A, 7B and 7C are top views of a coating surface of an applicator in accordance with different embodiments;

FIGS. 8A and 8B are illustrations of a region of a coating surface in accordance with different embodiments;

FIG. 9 is a perspective view of a support assembly for a stent to be used during a coating process;

FIGS. 10A, 10B, 11, 12A, 12B, 13A, 13B, 14A, 14B, 14C and 14D illustrate coating systems for coating a stent in accordance with various other embodiments of the present invention.

DETAILED DESCRIPTION

Implantable Medical Device

Figure 1:
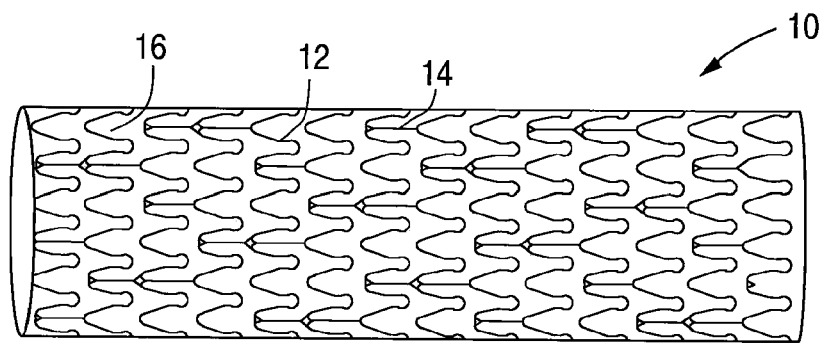
FIG. 1 illustrates a conventional stent.

Herein is disclosed a method and system for coating an implantable medical device. The implantable medical device can be a tubular device, such as a stent. In the interests of brevity, a method and system for coating a stent including a polymeric coating are described herein. However, one of ordinary skill in the art will understand that other medical devices having therapeutic capabilities can be coated using the system and method of the present invention.

Examples of implantable medical devices for the present invention include self-expandable stents, balloon-expandable stents, stent-grafts, sheaths and grafts (e.g., aortic grafts). The underlying structure of the device can be of virtually any design. The device can be made of a metallic material or an alloy such as, but not limited to, cobalt chromium alloy, stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The device can also be made partially or completely from bioabsorbable or biostable polymers.

System and Method for Coating an Implantable Medical Device

A coating system can be used to coat a stent by loading an applicator with a coating composition and transferring the coating composition from the applicator onto a stent. The coating composition can be applied directly to the surface of the stent, or to a previously applied layer of a coating material. In one embodiment, referring to FIG. 5, a coating system 20 for coating a stent 22 is illustrated to include a composition feeder 24 and an applicator 26. Feeder 24 is used to deposit a coating composition 28 onto applicator 26 adjacent to a lip 30 that holds the deposited coating composition, essentially creating a reservoir at one end of applicator 26. Coating composition 28 can include a solvent and a polymer dissolved in the solvent. Coating composition 28 can optionally include an active agent.

Applicator 26 has a porous region 32 that extends through a portion of the body of applicator 26. Porous region 32 is capable of conveying coating composition 28 by capillary action from lip 30 along the length of applicator 26. Capillary action (also known as "wicking") is the force resultant of adhesion, cohesion, and surface tension in liquids which are in contact with solids. For example, referring to FIG. 6, capillary action is the force which causes liquid 40 to be transported upward from a reservoir 42 into vertically oriented capillary tubes 44A, 44B, and 44C. Liquid 40 will rise to a stationary level, $Z\infty$, which is established by the balance between capillary action and gravitational force. $Z\infty$ can be determined by the following equation:

$$Z\infty = \frac{2\gamma\cos\theta}{\rho g r} \quad (1)$$

where $\gamma$ is the surface tension; $\theta$ is wetting angle of liquid 40; $\rho$ is the density of liquid 40; g is the gravitational force; and r is the capillary radius. The flow through capillary tubes 44A, 44B and 44C, dh/dt, can be determined by the following equation:

$$\frac{dh}{dt} = \frac{\gamma r\cos\theta}{4\eta h} - \frac{r^2 \rho g}{8\eta} \quad (2)$$

where $\gamma$ is the surface tension; r is the capillary radius; $\theta$ is wetting angle of liquid 40; $\eta$ is the viscosity of liquid 40; h is the height of liquid rise; $\rho$ is the density of liquid 40; and g is the gravitational force.

As noted above, the body of applicator 26 includes porous region 32 to receive the coating composition. Porous region 32 is configured so that capillary action through the region can load a layer 34 of coating composition 28 on a coating surface 36 of applicator 26. Representative examples of the thickness of layer 34 include about 2.5 microns to about 1000 microns. In one embodiment, the thickness is about 25 microns to about 100 microns.

Figure 5:
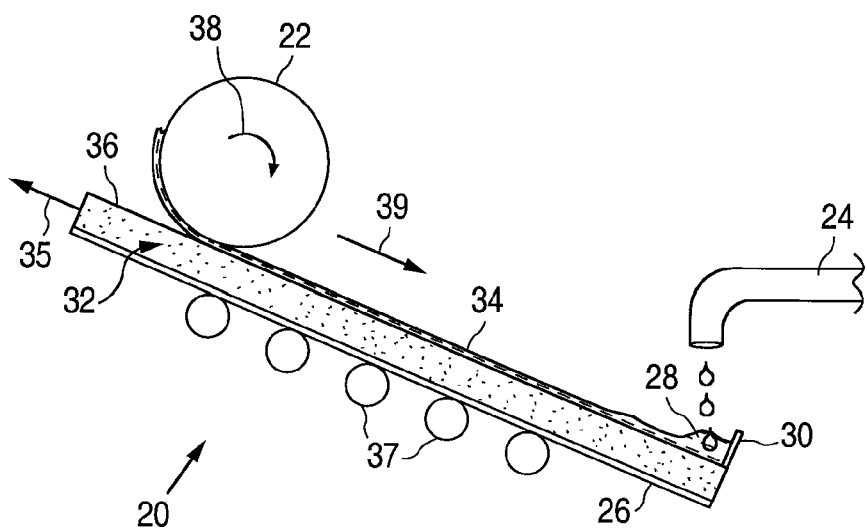
FIG. 5 illustrates a coating system for coating a stent in accordance with one embodiment of the present invention.
Figure 2:
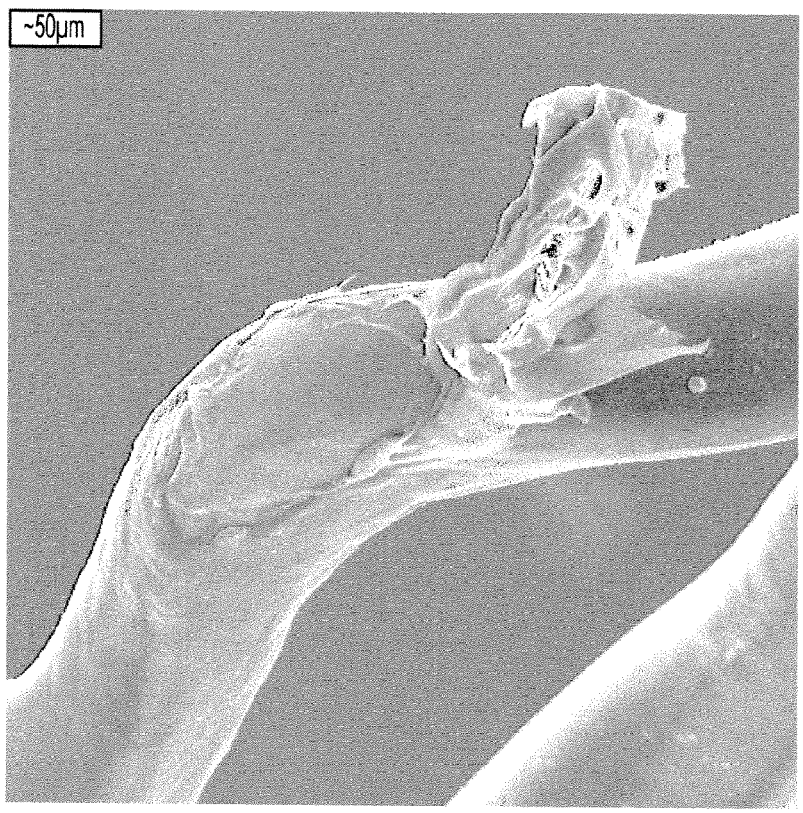
FIGS. 2, 3, and 4 are scanning electron microscope images of stent coatings with coating defects.
Figure 3:
Figure 4:

Once layer 34 is formed, stent 22 is rotated in a stationary position (i.e., rotated with no axial movement of stent 22 along applicator 26) or rolled along layer 34 (i.e., both rotational and axial movement of stent 22 along applicator 26) to transfer at least some of coating composition 28 to the outer surface of stent 22 or a coating pre-applied on stent 22. As shown in FIG. 5, the rotational motion of stent 22 is depicted by arrow 38. Rotational speed of stent 22 can be, for example, from about 1 rpm to about 50 rpm, more narrowly from about 1 rpm to about 20 rpm. In one embodiment, stent 22 is supported by a mandrel which is connected to a motor that provides rotational motion to stent 22 during the coating process.

In one embodiment, a portion of layer 34 is transferred to stent 22 while stent 22 is in a substantially horizontal position; in other words, while a longitudinal axis of stent 22 is parallel to or in the plane of the horizon. Coating stent 22 while in a horizontal position can be contrasted with a standard technique of dip coating a vertically positioned stent. When a stent is dip coated while in a vertical position, gravity causes some of the coating to gather at the lower portions of the stent, resulting in an uneven coating along the length of the stent. Coating a stent while in the horizontal position using the systems and methods of the present invention, on the other hand, can produce a more uniform coating along the length of the stent because gravity does not have as much influence on the coating composition after it is applied to the stent.

Porous region 32 of applicator 26 is an open pore system (i.e., a network of interconnected pores). Porous region 32 can have any suitable pattern on coating surface 36. Referring to FIG. 7A, which is a top view of coating surface 36, coating surface 36 can have a porous region 32A evenly distributed across the entire surface. Alternatively, referring to FIG. 7B, coating surface 36 can have a porous region 32B only disposed adjacent to the edges of coating surface 36. Coating surface 36 can also have a porous region 32C disposed only in the middle section of coating surface 36 (FIG. 7C). The patterns of porous regions 32B and 32C in FIGS. 7B and 7C, respectively, can be used to selectively apply a coating composition along the body of a stent. For example, if stent 22 is long enough to extend across substantially all of the width of coating surface 36 so that the ends of stent 22 are positioned across a portion of porous region 32B, then the pattern of porous region 32B of FIG. 7B will selectively apply the coating to the end regions of the stent as opposed to the middle segment. The pattern of porous region 32C of FIG. 7C, on the other hand, can be used to selectively coat the middle segment of stent 22.

Porous region 32 of applicator 26 can include pores having any suitable shape so that porous region 32 is capable of loading coating composition 28 by capillary action. In one embodiment, pores 50A can have irregular shapes, as illustrated by FIG. 8A. In another embodiment, referring to FIG. 8B, pores 50B of porous region 32 all have a uniform shape such as spherical or cylindrical shape (i.e., circular in a cross section). One advantage of using a porous substrate having pores with a uniform shape is that the porous substrate can act as a filter for the coating composition. For example, the porous substrate can filter out impurities that have particle sizes that are larger than the pores of the porous substrate. Also, if the coating composition includes drug particles, a porous region with uniform pores can trap and filter out those particles that are larger than the pore size.

Porous region 32 of applicator 26 can include pores having any suitable size and have any suitable porosity so that porous region is capable of transporting the coating composition by capillary action. In one embodiment, porous region 32 includes pores having an average pore radius of about 0.1 microns to about 1000 microns, more narrowly, about 0.25 microns to about 90 microns. In another embodiment, porous region 32 has a porosity of about 20% to about 60%, more narrowly, about 40% to about 45%. Porosity is the total volume of pores in the porous region divided by the total volume of the substrate in the porous region. The average pore radius and porosity can be provided by the manufacturer of the selected material, or alternatively can be determined by standard techniques such as mercury penetration porosimetry, or other techniques as described in Gregg et al., Adsorption, Surface Area, and Porosity, $2^{nd}$ ed. (Academic, London, 1982).

Applicator 26 can be made of a porous material that is "non-stick," having a low friction coefficient. The material should be resistant to solvents (e.g., organic solvents such as acetone) and heat, which may be directed onto applicator 26 during the coating process. In one embodiment, applicator 26 is made of a rigid material. A rigid material, as opposed to a pliable or malleable material, can advantageously provide a coating surface that can resist the pressure applied by stent 22 during the application process. This resistance allows for a more uniform coating layer to be transferred to stent 22. Representative examples of materials that can be used for applicator 26 include ceramic materials (such as a suitable brand available from Refractron Technologies Corp., Newark, N.Y.), and polymeric materials such as polyethylene (e.g., Tyvek®, available from DuPont, Wilmington, Del.), and polytetrafluoroethylene (PTFE) (e.g., Teflon®, available from DuPont, Wilmington, Del., or International Polymer Engineering, Inc., Tempe, Ariz.). Ceramic is an especially suitable material because ceramic can transport both aqueous and hydrophobic compositions and is highly resistant to heat and organic solvents.

In one embodiment, referring to FIG. 5, coating surface 36 is completely or substantially flat, and without any curvatures along the length or width of coating surface 36. By providing a flat coating surface 36, the thickness of the coating applied to stent 22 can be substantially uniform.

In some embodiments, applicator 26 can be capable of moving in a linear direction towards stent 22 as indicated by arrow 35 to deposit coating composition 28 on stent 22. Applicator 26 can be integrated with a plurality of rollers 37 to provide axial motion. Applicator 26 can be moved at about 1 mm/second to about 30 mm/second, for example about 6 mm/second.

In one embodiment, the movement of applicator 26 will cause stent 22 to rotate by frictional force such that a motor for rotating stent 22 is not needed. Feeder 24 can be any suitable apparatus configured to deposit coating composition 28 onto applicator 26. To realize greater process efficiency, coating composition 28 can be introduced into the process by means of individually metered, continuous mass flow streams through feeder 24. The flow rate of coating composition 28 from feeder 24 can be from about 0.2 mg/second to about 10 mg/second, for example about 5.0 mg/second.

As coating composition 28 is applied to stent 22, coating composition 28 should be in a substantially free-flowing or liquid form. The viscosity of coating composition 28 when applied onto stent 22 can be at about 10 centipoises at ambient temperature and pressure to about 100 centipoises at ambient temperature and pressure. The consistency of the coating composition can affect the capillary action process and how the composition is received by stent 22.

Stent 22 can be supported by a mandrel during the coating process. The mandrel can be used to position stent 22 in close proximity to or in contact with coating surface 36. The mandrel is configured to allow stent 22 to be rotated about a central longitudinal axis of stent 22 during the coating process. The mandrel can also be configured so that stent 22 can be rolled towards lip 30 (i.e., moved in a linear direction as shown by arrow 39). The mandrel can have any design that is suitable to support stent 22 during the coating process. Referring to FIG. 9, stent 22 can be integrated with a mandrel 60 that includes a spring-loaded plug 62 positioned at a distal end of a stem 64. Plug 62 can be circular in cross-section making contact with the inner surface of stent 22. Plug 62 can also have other shapes or designs so long as the intended function of plug 22 is performed. Plug 62 can have an almost equivalent diameter to the inner diameter of stent 22 as positioned on mandrel 60. By way of example, the outer diameter of the plug 62 can be from about 1 mm to about 8 mm.

Plug 62 can be made of materials that are rigid or semi-pliable. In some embodiments, the material can be a "non-stick" material having a low friction coefficient and should be resistant to solvents and heat, which may be directed onto plug 62 during the coating process. Stent 22 can rotate with respect to plug 62 or can be crimped tightly on plug 62 such that the rotation of plug 62 causes stent 22 to rotate. Representative examples of materials that can be used for plug 62 include polyurethanes, polyetheretherketone, polytetrafluoroethylene (e.g., Teflon®), Delrin™, Rulon™, Pebax™, Kynar™, Solef™, fluorinated ethylene-propylene copolymer, poly(vinylidene fluoride-co-chlorotrifluoroethylene), poly(vinyl fluoride), polyesters such as poly(ethylene terephthalate), nylon, stainless steel, titanium alloys, cobalt-chromium alloys, ceramics, metallic carbides, inorganic carbides, and nitrides.

Instead of plug 62, stent 22 can also be held by other support designs. For example, stent 22 can be supported by two plugs, one at each end of stent 22. The two plugs in this type of support apparatus could be connected by an internal mandrel. Alternatively, the two plugs could be unconnected having their relative orientation maintained by an external fixture. The two end plugs can be conical in shape, and therefore, contact stent 22 at contact points at the end struts.

In one embodiment, coating system 20 includes a temperature controller for heating or cooling coating composition 28. The temperature controller can be used to heat or cool coating composition 28 in order to produce and maintain a coating consistency that is suitable for depositing a coating on stent 22. Control over the temperature of coating composition 28 can be especially important for providing adequate conditions for the capillary action of the composition. For instance, the capillary action can be less effective as coating composition 28 becomes more viscous. The temperature controller can include any suitable apparatus for heating or cooling the coating composition, and can be in communication with any suitable component of coating system 20. In one embodiment, applicator 26 is in communication with the temperature controller so that the temperature controller can modify the temperature of coating composition 28 during the coating process. In another embodiment, mandrel 60 is in communication with the temperature controller so that the temperature controller can modify the temperature of stent 22 during the coating process.

Other embodiments of capillary action applicators will be described hereinafter. In some embodiments, these applicators can have the same property and characteristic as applicator 26. For example, these applicators can have the same porosity and be made from the same materials described above, e.g., ceramics. Referring to FIG. 10A, a coating system 70 including an applicator 72 and a reservoir 74 can be used to apply a layer of a composition to stent 22. Applicator 72 has a porous region 76 that extends at least from the bottom to the top or upper surface of applicator 72. A portion of applicator 72 is partially submerged in a coating composition 78 disposed in reservoir 74 so that at least a portion of porous region 76 of applicator 72 is in contact with coating composition 78. Capillary action through porous region 76 of applicator 72 causes coating composition 78 to be removed from (i.e., wicked from) reservoir 74 and transported through the body of applicator 72 until a layer 80 is formed on a coating surface 82 (i.e., the upper outer surface of applicator 72). Although FIGS. 10A and 10B illustrate an applicator 72 that has porous region 76 that extends through the entire body of applicator 72, porous region 76 can have pores selectively distributed in the body of applicator 72 (e.g., akin to coating surface 36 of FIGS. 7B and 7C) as long as porous region 76 is able to transport coating composition 78 from reservoir 74 to coating surface 82.

A portion of layer 80 can then be transferred to stent 22 by rolling stent 22 along coating surface 82. Stent 22 can be supported by a mandrel and positioned so that stent 22 is in close proximity to or in contact with coating surface 82 as stent 22 is rolled along coating surface 82. A motor can be used to drive stent 22 along coating surface 82.

The viscosity of coating composition 78 in reservoir 74 can be at about 10 centipoises to about 100 centipoises at ambient temperature and pressure. Coating system 70 can include a temperature controller to control the viscosity of coating composition 78. Any suitable component of coating system 70 can be in communication with the temperature controller, such as the mandrel supporting stent 22, applicator 72 and/or reservoir 74.

By positioning applicator 72 in reservoir 74, there can be a continuous loading process. In other words, each time after a portion of coating composition 78 is transferred from coating surface 82 to stent 22, capillary action loads coating surface 82. In one embodiment, applicator 72 is movable within reservoir 74 so that as coating composition 78 is removed from reservoir 74, applicator 72 is lowered into reservoir 74. By allowing applicator 72 to be lowered into reservoir 74 during the coating process, applicator 72 can maintain contact with coating composition 78 disposed in reservoir 74. Applicator 72 can be lowered during the coating process or the rolling of stent 22. Alternatively, applicator 72 can be lowered between coating applications. Stent 22 can be rotated at least one full cycle followed by lowering of applicator 72. In some embodiments, an amount of composition can be applied to stent 22, followed by drying of the composition or removal of the solvents, followed by lowering of applicator 72 and re-application of the composition. In another embodiment, coating system 70 includes a feeder or pump (not shown) that is configured to deliver coating composition 78 into reservoir 74 as coating composition 78 is transferred onto one or more stents. The feeder or pump can be used to maintain a sufficient level of coating composition 78 within reservoir 74. Reservoir 74 can also include a composition level indicator that is capable of measuring the level of coating composition 78, and indicating when the level is too low. Such a level indicator can be in communication with the feeder or pump in order to automate the process.

The loading of coating surface 82 can be enhanced by application of a pressure. A vacuum apparatus can be used to drawn composition 78 to coating surface 82. For example, FIG. 10A can be a closed chamber such that the top region of the chamber, opposing reservoir 74, is in communication with a vacuum system. Alternatively, reservoir 74 can be pressurized to encourage coating composition 78 to be conveyed from reservoir 74 to coating surface 82. In one embodiment, a gas such as filtered air or an inert gas (e.g., nitrogen) is pumped into reservoir 74 to increase the pressure of reservoir 78.

Figure 11:
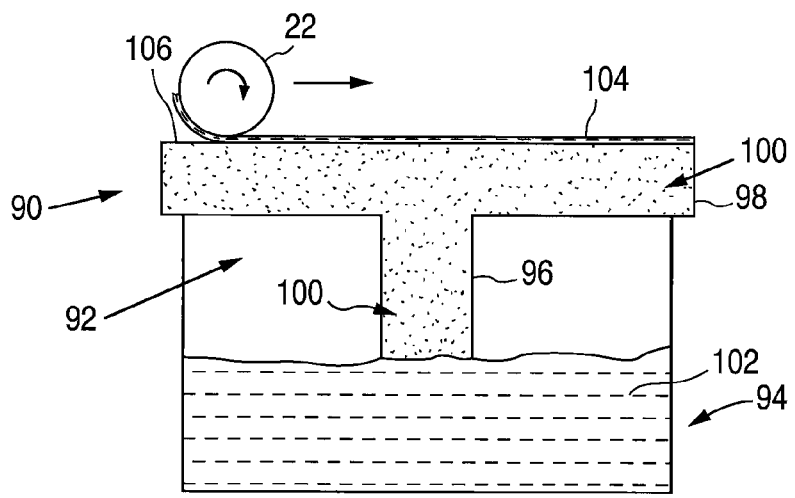

In another embodiment of the present invention, referring to FIG. 11, a coating system 90 including an applicator 92 and a reservoir 94 can be used to apply a layer of composition to stent 22. Applicator 92 includes a first section 96 and a second section 98. Each of the first and second sections 96 and 98 has a porous region 100 disposed along the body of first and second sections 96 and 98 for transporting a coating composition 102 from reservoir 94 to a coating surface 106. First section 96 can act as the primary conveyer of coating composition 102 from reservoir 94. Additionally, first section 96 can be sized or otherwise configured so that first section 96 does not extend across or cover the entire reservoir 94. As best illustrated by FIG. 11, an open space between coating composition 102 and the bottom of second section 96 is therefore provided. By having a first section 96 that does not extend across the entire reservoir 94, less coating composition is necessary to load porous region 100. Also, by configuring applicator 92 to produce an open space, a gas can be more easily delivered to reservoir 94 via the open space, and the increased pressure can be more uniformly delivered to composition 102.

Second section 98, on the other hand, can be sized or otherwise configured so that second section 98 provides a wide platform for coating stents. For example, as shown in FIG. 11, second section 98 can have a length (and width) that is sufficiently longer than reservoir 94 so as to be able to accommodate any number of stents. A sealant can be applied to the area where reservoir 94 and second section 98 contact each other. By sealing this area, if a gas is delivered to reservoir 94, the gas can more effectively increase the pressure of reservoir 94.

The respective porous regions of first and second sections 96 and 98 can have the same or different porosity and average pore radii. In one embodiment, porous regions 100 of first and second sections 96 and 98 have substantially the same porosity, but porous region 100 of first section 96 has pores with a lesser average pore radius than the pores of porous region 100 of second section 98. Smaller pores of first section 96 can convey coating composition 102 from reservoir 94 to a greater height at a faster rate. Then, the larger pores of second section 98 can provide for an ultra-thin layer of coating composition 102 along coating surface 106.

First section 96 of applicator 92 is partially submerged in coating composition 102 disposed in reservoir 94 so that at least a portion of porous region 100 of first section 96 is in contact with coating composition 102. As first section 96 remains partially submerged, capillary action along porous region 100 of first section 96 causes coating composition 102 to be removed from reservoir 94 and into the body of first section 96. After a sufficient loading time, coating composition 102 is transported to second section 98 by capillary action, and ultimately a layer 104 is formed on coating surface 106. Stent 22 can be supported by a mandrel so that stent 22 is in close proximity to or in contact with coating surface 106. Coating composition 102 can then be transferred to stent 22 by rolling stent 22 along coating surface 106 after layer 104 has been loaded with coating composition 102. First and second sections 96 and 98 can be connected in any way that does not interfere with the capillary action process. For example, first and second sections 96 and 98 can be connected with a "tongue and groove" configuration.

Figure 12A:
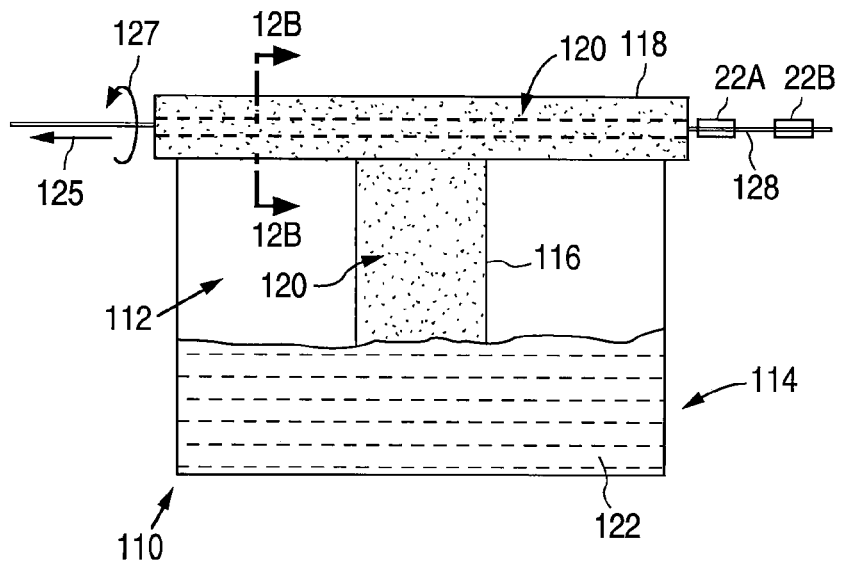
Figure 12B:
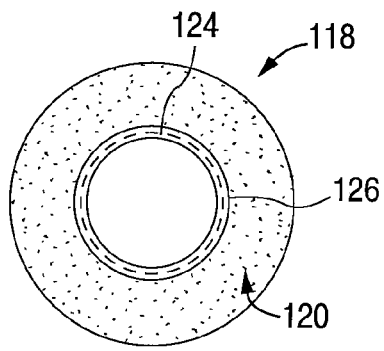

In another embodiment of the present invention, referring to FIGS. 12A and 12B, a coating system 110 including an applicator 112 and a reservoir 114 can be used to apply a layer of a coating composition stent 22. Applicator 112 can include a first section 116 and a second section 118. First and second sections 116 and 118 have a porous region 120 disposed in the body of each section for transporting the composition from reservoir 114 by capillary action. First section 116 of applicator 112 is partially submerged in a coating composition 122 disposed in reservoir 114 so that at least a portion of porous region 120 of first section 116 is in contact with coating composition 122. As first section 116 remains partially submerged, capillary action along porous region 120 of first section 116 causes coating composition 122 to be removed from reservoir 114 and into the body of first section 116. Second section 118 can be configured as a tubular substrate, having a hollow, longitudinal bore. The inner bore of the tube can have a radius of curvature that is about equal to a radius of curvature of stent 22. Coating composition 122 is transferred from reservoir 114 to first section 116, and then to second section 118 by capillary action. A layer 124 of coating composition 122 is then formed on a coating surface 126 (i.e., the inner surface of second section 118).

Coating composition 122 deposited on coating surface 126 can be transferred to stent 22 by inserting stent 22 into the bore of second section 118, and then removing stent 22 from the bore. During insertion and/or removal of stent 22, the outer surface of stent 22 should be in close proximity or in contact with coating surface 126 so that coating composition 122 is transferred to stent 22. Stent 22 can be inserted and removed from the same side of the bore to deposit the coating composition. Alternatively, as shown in FIG. 12A, one or more stents 22A and 22B can be supported by a mandrel 128 that is inserted and taken through the entire length of the bore (e.g., in a linear direction as shown by arrow 125). Stents 22A and 22B can be positioned at a distance from each other as they are taken through the bore in order to give applicator 112 a chance to reload coating surface 126 before the next stent 22 in the series reaches coating surface 126. Furthermore, in order to provide a more uniform coating on stent 22, stent 22 can be rotated while positioned within the bore of second section 118 as shown by arrow 127. In order to transfer the composition from second section 118 to stent 22, the diameter of the bore of second section 118 should be only be slightly greater than the diameter of stent 22. By way of example, the inner diameter of the bore of second section 118 can be from about 0.1 mm to about 0.01 mm larger than the outer diameter of stent 22, for example, 0.01 mm larger. Since stent 22 is radially expandable, when referring to the diameter of stent 22, the measurement is the diameter of stent 22 during the coating process.

As above, a portion of layer 124 can be transferred to stent 22 while stent 22 is in a substantially horizontal position; in other words, while a longitudinal axis of stent 22 is parallel to or in the plane of the horizon. Coating stent 22 while in the horizontal position can produce a uniform coating along the length of stent 22 because gravity does not have as much influence on the coating composition after it is applied to the stent.

Figure 13A:
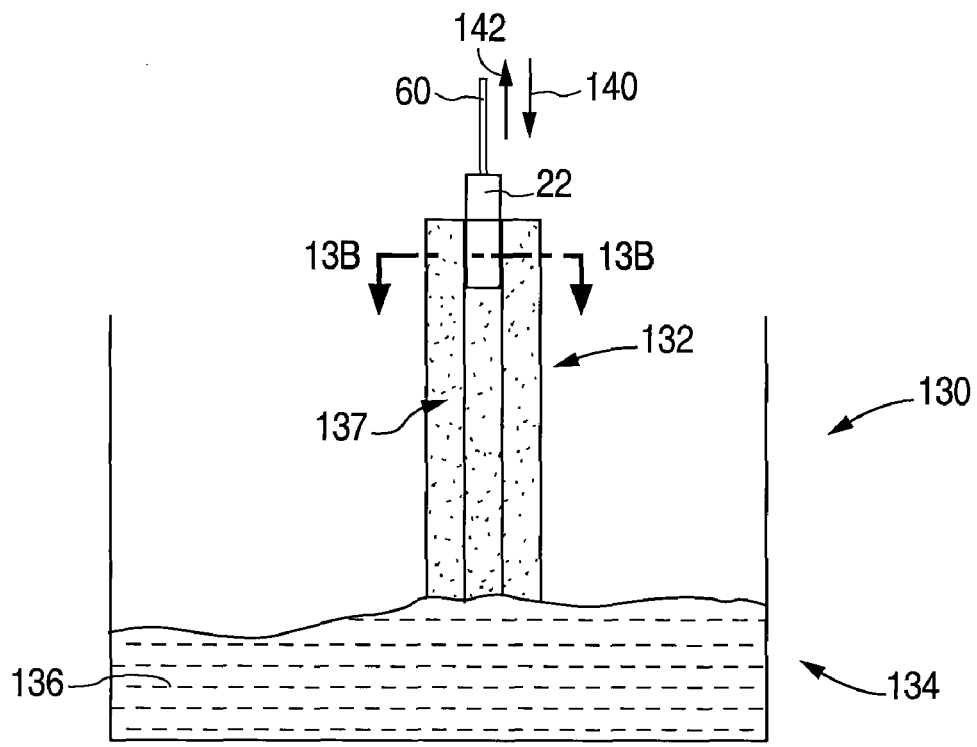
Figure 13B:
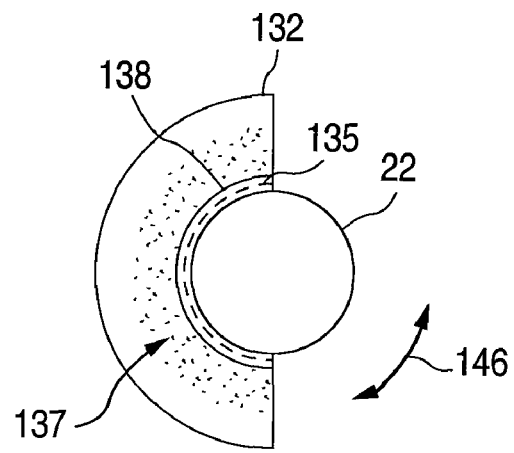

In another embodiment of the present invention, an applicator having a body shaped like a tube or a half-tube can be inserted into a reservoir while in a completely or substantially vertical position in order to load the applicator with a coating composition. Referring to FIGS. 13A and 13B, a coating system 130 can include an applicator 132 and a reservoir 134. Applicator 132 includes a porous region 137 and is configured as a half-tube. Applicator 132 is partially submerged in a coating composition 136 disposed in reservoir 134 so that at least a portion of porous region 137 is in contact with a coating composition 136. As applicator 132 remains partially submerged, capillary action through porous region 137 of applicator 132 causes coating composition 134 to be removed from reservoir 134 into the body of applicator 132, and eventually to deposit a layer 135 of coating composition 136 on coating surface 138.

Coating composition 136 deposited on coating surface 138 can be transferred to stent 22 by inserting stent 22 into the half-bore of applicator 132, and then removing stent 22 up and down as shown by arrows 140 and 142. Stent 22 can be supported by mandrel 60 during the insertion and removal. Stent 22 can be inserted up to any suitable distance into the half-bore. To enhance coating uniformity, stent 22 can be rotated while in the half-bore as shown by arrow 146.

As with other embodiments of the present invention, applicator 132 can be positioned in a horizontal orientation so that a portion of layer 135 can be transferred to stent 22 while stent 22 is in a substantially horizontal position. For example, applicator 132 can replace second section 118 of applicator 112 of FIG. 12A. In such a configuration, coating surface 138 of applicator 132 could be oriented to face away from reservoir 134.

In another embodiment of the present invention, referring to FIGS. 14A-14D, a coating system 150 includes an applicator 152 and a reservoir 154. Coating system 150 can be used to apply a layer of composition to the outer surface of stent 22. Applicator 152 includes a tubular shell 156 that houses a plurality of absorbent fibers 158. Tubular shell 156 is pliable and can be compressed by applying sufficient radial force as shown by arrows 160. Tubular shell 156 can be made of any suitable material that is pliable, such as but not limited to elastic polymeric materials such as rubber, or plastic foam such as polyethylene foam.

Fibers 158 can have any suitable configuration that allows fibers 158 to transport a coating composition by capillary action and transfer the coating composition to stent 22. Fibers 158 can be configured to have one absorbent filament, or, as shown in FIGS. 14C and 14D, fibers 158 can be configured to include a network of filaments or capillaries 162. If fiber 158 has multiple filaments, the total flow through each fiber is given by the sum of individual flows of each capillary 162 in each fiber. Capillaries 162 can be distributed along the length of fibers 158 in a parallel fashion, or can be woven or braided with each other.

Fibers 158 can be formed of any suitable material that is able to transport a coating composition by capillary action, and otherwise function as disclosed herein. The material used to make fibers 158 should be sufficiently elastic so that fibers 158 do not fracture or otherwise fail when tubular shell 156 is collapsed or compressed as further described below. Furthermore, the material selected for fibers 158 should be compatible with the components of the coating composition, such as the solvent used in the coating composition. Examples of materials that can be used to construct fibers 158 include those materials disclosed in U.S. Pat. No. 5,972,505, among others. Representative examples of materials include carbon; cotton; polyolefins such as polypropylene and polyethylene; polyesters such as poly(ethylene terephthalate); nylon, such as nylon 66 or nylon 6; cellulose esters such as cellulose triacetate or cellulose diacetate; binary blends of cellulose esters with aliphatic polyesters or aliphatic-aromatic copolyesters as well as ternary blends of cellulose esters with aliphatic polyester/polyacrylates, aliphatic polyesters/polyvinyl acetates/aliphatic polyesters/polyvinyl alcohol, aliphatic polyesters/polyvinyl chloride, aliphatic polyesters/polycarbonate, aliphatic polyesters/polyvinyl acetate-polyethylene copolymer, aliphatic polyesters/cellulose ethers, aliphatic polyesters/nylon, aliphatic-aromatic copolyesters/polyacrylates/aliphatic-aromatic copolyesters/polyvinyl acetates, aliphatic-aromatic copolyesters/polyvinyl alcohol, aliphatic-aromatic copolyesters/polyvinyl chloride, aliphatic-aromatic copolyesters/polycarbonate, aliphatic-aromatic copolyesters/polyvinyl acetate-polyethylene copolymer, or aliphatic-aromatic copolyesters/cellulose ethers, and aliphatic-aromatic copolyesters/nylon.

Fibers 158 can be formed by any suitable method. For example, by the methods described in U.S. Pat. No. 5,972,505 and Neimark et al., Hierarchical Pore Structure and Wetting Properties of Single-Wall Carbon Nanotube Fibers, Nano Letters, 3(3):419-23 (2003).

In operating coating system 150, fibers 158 can be partially submerged in a coating composition disposed in reservoir 154. As fibers 158 remain partially submerged, capillary action along the length of fibers 158 causes the coating composition to be removed from reservoir 154 into fibers 158. Coating composition 159 can be transferred to stent 22 by inserting stent 22 into tubular shell 156 and compressing tubular shell 156 so that fibers 158 transfer coating composition 159 to the outer surface of stent 22. Stent 22 can be inserted up to any suitable distance into tubular shell 156. If stent 22 is to be coated along the entire length of stent 22, stent 22 should be completely inserted into tubular shell 156. After stent 22 has been inserted at the selected distance, tubular shell 156 should be compressed to a sufficient radius so that fibers 158 are in close proximity or in contact with the outer surface of stent 22. To enhance coating uniformity, fibers 158 can be sized and/or positioned so that there are few or no gaps 164 between fibers 158 and the stent surface. Additionally, stent 22 can be rotated while fibers 158 are compressed against the stent surface to enhance coating uniformity.

Figure 15A:
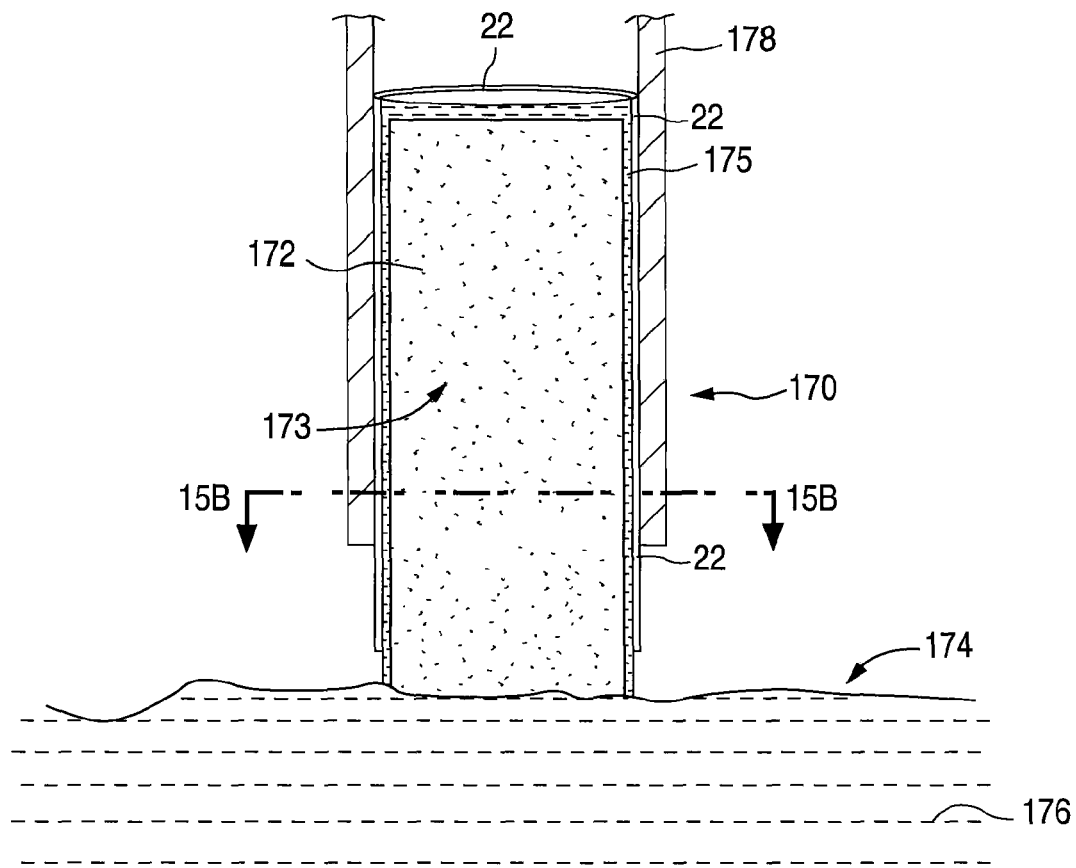
FIGS. 15A, 15B, 16A and 16B illustrate coating systems for coating an inner surface of a stent in accordance with other embodiments of the present invention.
Figure 15B:
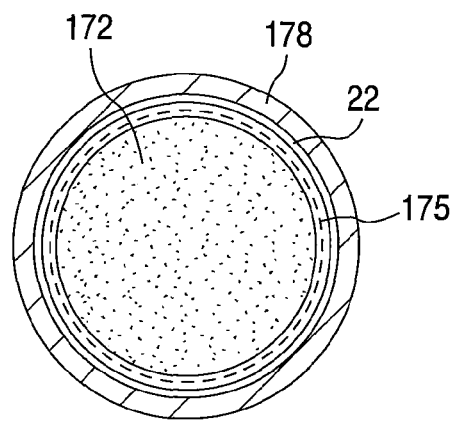

In another embodiment, a system is provided for coating an inner surface of stent 22. Coating just the inner surface can be advantageous for the delivery of therapeutic agents to the blood system to prevent thrombosis or promote rapid reendothelialization. For instance, certain drugs may effectively treat cardiovascular injuries when carried away by the blood flow to an area adjacent to the site of stent implantation. These drugs, for example, may be used to treat "edge restenosis." Referring to FIGS. 15A and 15B, a coating system 170 can include an applicator 172 and a reservoir 174. Applicator 172 includes a porous region 173 and has a cylindrical shape. Applicator 172 has porous region 173 disposed in the body of applicator 172 for transporting the composition from reservoir 174. Applicator 172 is partially submerged in a coating composition 176 disposed in reservoir 174 so that at least a portion of porous region 173 is in contact with coating composition 176. As applicator 172 remains partially submerged, capillary action through porous region 173 of applicator 172 causes coating composition 176 to be removed from reservoir 174 into the body of applicator 172, and eventually to form a layer 175 on the outer surface of applicator 172.

Stent 22, in turn, can be supported in a tube 178. Tube 178 should have an inner diameter that allows tube 178 to grip and mask a portion of the outer diameter of stent 22. Applicator 172 can be sized to provide an effective circumference to deliver a coating composition to the inner surface of stent 22. By way of example, the outer diameter of applicator 172 can be about 0.1 mm to about 0.01 mm, for example, 0.01 mm less than the inner diameter of stent 22. In one embodiment, applicator 172 and/or tube 178 are in communication with a temperature controller.

Figure 16A:
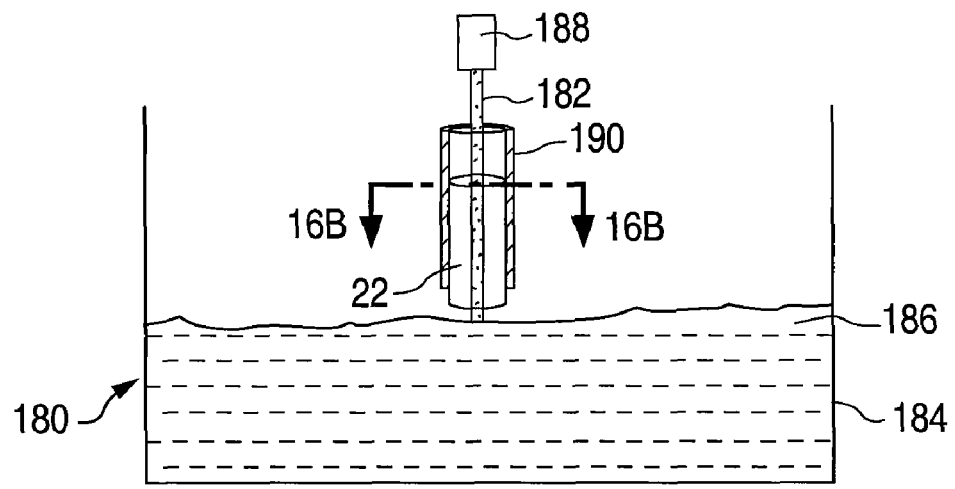
Figure 16B:
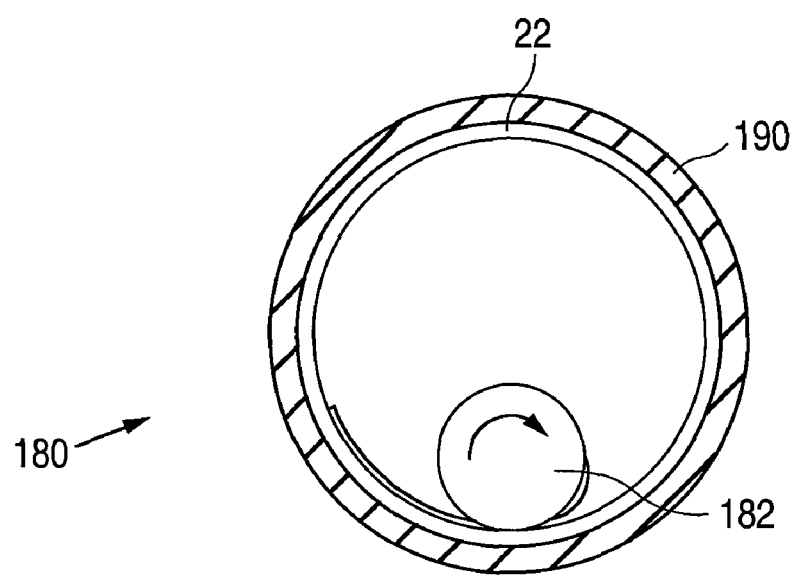

Referring to FIGS. 16A and 16B, a coating system 180 is provided for coating the inner surface of a stent 22 including an applicator 182 and a reservoir 184 for holding a coating composition 186. Applicator 182 includes a porous region disposed through the body of applicator 182. Applicator 182 is integrated with a grip 188 that is substantially free from pores so that applicator 182 can be handled without contacting wet composition. Stent 22, in turn, can be supported in a tube 190. The outer surface of applicator 182 can be coated with a wet coating by capillary action before contacting the inner surface of stent 22. Applicator 182 can then be rolled around the inner circumference of stent 22. As with the above described embodiments, coating system 180 can include a temperature controller for heating or cooling coating composition 186 during the coating process.

Multiple repetitions for applying the coating composition can be performed using the system and method of the present invention. As noted above, selective components of the coating systems as described herein can be disposed in a pressure chamber so that the pressure can be altered at any time during the coating process. The amount of composition applied by each repetition, can be about 1 microgram/cm$^2$ (of stent surface) to about 100 milligrams/cm$^2$, for example about 100 micrograms/cm$^2$ per application. Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds.

Any suitable number of repetitions of applying the composition followed by removing the solvent(s) can be performed to form a coating of a desired thickness or weight. The coating process as described herein can be used to form a coating on the stent having a thickness of about 0.1 microns to about 100 microns, more narrowly, about 0.5 micron to about 20 microns.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

The stent can be at least partially preexpanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

Coating Composition

As noted above, the coating composition can include a solvent and a polymer dissolved in the solvent, and optionally an active agent. Representative examples of polymers that can be used to coat a medical device in accordance with the present invention include ethylene vinyl alcohol copolymer (commonly known by the generic name EVOH or by the trade name EVAL); poly(hydroxyvalerate); poly(lactic acid) including poly(L-lactic acid), poly(D-lactic acid) and poly(D, L-lactic acid), and copolymers thereof such as poly(lactide-co-glycolide); polycaprolactone; poly(hydroxybutyrate); poly(hydroxybutyrate-co-valerate); polydioxanone; polyorthoester; polyanhydride; poly(glycolic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride, polyvinylidene chloride poly(vinylidene fluoride-co-hexafluoropropene), and poly(vinylidene fluoride-co-chlorotrifluoroethylene); polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect for the subject. For example, the agent can be for enhancing wound healing in a vascular site or improving the structural and elastic properties of the vascular site.

By using the system and method of the present invention, the same active agent can be applied to the inner and outer surfaces of stent 22. Alternatively, different active agents can be applied to the two surfaces. For example, the outer surface of stent 22 can be coated with a drug that is capable of treating restenosis. The inner surface of stent 22, on the other hand, can be coated with an angiogenic drug.

Examples of agents include antiproliferative substances such as actinomycin D, or derivatives and analogs thereof (manufactured by Sigma-Aldrich 1001 West Saint Paul Avenue, Milwaukee, Wis. 53233; or Cosmegen® available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., Taxol® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is pemirolast potassium. Other therapeutic substances or agents which may be appropriate include alpha-interferon, genetically engineered epithelial cells, dexamethasone and rapamycin and structural derivatives or functional analogs thereof, such as 40-O-(2-hydroxy)ethyl-rapamycin (known as everolimus, available from Novartis), 40-O-(3-hydroxy)propyl-rapamycin, 40-O-[2-(2-hydroxy)ethoxy]ethyl-rapamycin, and 40-O-tetrazole-rapamycin.

EXAMPLES

Some embodiments of the present invention are illustrated by the following Examples. The Examples are being given by way of illustration only and not by way of limitation. The parameters and data are not be construed to unduly limit the scope of the embodiments of the invention.

Example 1

A 18 mm Vision stent (available from Guidant Corporation) was placed over a solid mandrel to fully support the stent along the length of the stent. A coating composition was prepared. The coating composition included 3% (w/w) poly (lactic acid) and 97% acetone (w/w). The coating composition was transferred to a stainless steel cell to be used as a reservoir. A two inch diameter porous ceramic disk with an average pore radius of 6 μm (available from Refractron Technologies Corp., Newark, N.Y.) was partially submerged in the coating composition held by the reservoir. A thin, wet film of the coating composition was quickly formed on the upper surface of the disk. The mounted stent was rolled over the upper surface of the ceramic disk by hand at one revolution per second to transfer a portion of the film to the outer surface of the stent. The stent was weighed after the application, and it was determined that about 25 μg to about 30 μg of coating composition had been applied to the stent.

Example 2

A 18 mm Vision stent (available from Guidant Corporation) was placed over a solid mandrel to fully support the stent along the length of the stent. The coating composition of Example 1 was transferred to a stainless steel cell to be used as a reservoir. A two inch porous ceramic disk with an average pore radius of 6 μm (available from Refractron Technologies Corp., Newark, N.Y.) was partially submerged in the coating composition held by the reservoir. A thin, wet film of the coating composition was quickly formed on the upper surface of the disk. The mounted stent was rolled over the upper surface of the ceramic disk by hand to transfer a portion of the film to the outer surface of the stent. The rolling process was repeated for three additional times. The stent was weighed after the application, and it was determined that about 75 μg of coating composition had been applied to the stent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A method for coating an implantable medical device, comprising:
    providing an apparatus including a reservoir portion holding a coating composition, an applicator portion including a coating surface and a porous region in fluid communication with the coating surface and coating composition;
    regulating the pressure over the porous region to control flow of coating composition from the reservoir portion to the coating surface; and
    coating the medical device by placing the medical device in close proximity to or in contact with the coating surface of the applicator;
    wherein the apparatus further includes a sealed space separating a portion of the coating composition in the reservoir portion from the applicator portion and
    the regulating step further includes the step of supplying a pressurizing gas to the sealed space so as to control the rate at which coating composition flows from the reservoir to the coating surface.

2. The method of claim 1, wherein the porous region has a porosity of between about 20% and 60%.

3. A method for coating an inner surface of a stent, comprising the steps of:
    providing an applicator having a cylindrical shape and a porous region in fluid communication with an outer surface of the applicator and a reservoir of coating composition;
    supporting the stent within a tube including gripping the stent with the tube; and
    coating the stent including placing the stent over the applicator using the tube so that the stent luminal surface is in close proximity to, or in contact with the outer surface of the applicator;
    the providing step further including partially submerging the applicator in a reservoir of coating composition; and
    the coating step including lowering the applicator into the reservoir as coating composition is deposited onto the luminal surface.

4. The method of claim 3, the supporting step further including masking an abluminal surface of the stent with the tube.

5. The method of claim 3, further including the step of controlling the viscosity of the coating composition by supplying heat to the applicator and/or reservoir.

6. A method of coating a stent having a center portion and end, comprising:
    providing a reservoir holding a coating composition, an applicator including a coating surface having a first portion and a second portion, and a porous region in fluid communication with the coating composition and terminating at only the first portion of the coating surface;
    conveying coating composition to the coating surface from the reservoir by way of the porous region, whereby coating composition is disposed only at the first portion; and
    coating only one of the center portion and end of the stent including placing the stent adjacent to or in contact with both the first portion and second portion of the coating surface.

7. The method of claim 6, wherein the coating surface is substantially planar and the first portion corresponds to a centrally located portion of the coating surface,
    wherein the coating step includes rolling the stent over the coating surface whereby only the center portion of the stent comes in contact with coating composition.

8. The method of claim 6, wherein the coating surface is substantially planar and the second portion corresponds to a centrally located portion of the coating surface, and
    wherein the coating step includes rolling the stent over the coating surface whereby only the end of the stent comes in contact with coating composition.

* * * * *